United States Patent [19]

Shalaby et al.

[11] Patent Number: 5,082,925

[45] Date of Patent: Jan. 21, 1992

[54] HOMOPOLYMERS AND COPOLYMERS OF SALICYLATE LACTONES

[75] Inventors: Shalaby W. Shalaby, Lebanon; Donald F. Koelmel, Glen Gardner, both of N.J.; Steven Arnold, New Hope, Pa.

[73] Assignee: Ethicon, Inc., Somerville, N.J.

[21] Appl. No.: 568,392

[22] Filed: Aug. 16, 1990

[51] Int. Cl.$^5$ ............................................. C08G 63/08
[52] U.S. Cl. ...................................... 528/354; 528/480
[58] Field of Search ................................. 528/354, 480

[56] References Cited

U.S. PATENT DOCUMENTS

| | | | |
|---|---|---|---|
| 2,956,064 | 10/1960 | Kagan et al. | 549/267 |
| 4,190,720 | 2/1980 | Shalaby et al. | 528/354 |
| 4,441,496 | 4/1984 | Shalaby et al. | 128/335.5 |
| 4,470,416 | 9/1984 | Kafrawy et al. | 128/335.5 |
| 4,810,775 | 3/1989 | Bendix et al. | 528/480 |
| 4,891,263 | 1/1990 | Kotliar et al. | 428/225 |
| 4,920,203 | 4/1990 | Tang et al. | 525/409 |

*Primary Examiner*—John Kight, III
*Assistant Examiner*—Shelley A. Wright
*Attorney, Agent, or Firm*—Matthew S. Goodwin

[57] ABSTRACT

Poly(1,4-benzodioxepin-2,5-(3-H)dione), poly(1,4-benzodioxepin-2,5-(3-H, 3-methyl)dione), and copolymers of 1,4-benzodioxepin-2,5-(3-H)dione or 1,4-benzodioxepin-2,5-(3-H, 3-methyl)dione and at least one of: a) glycolide, b) (L-)lactide, c) an alkylene carbonate, d) p-dioxanone, e) e-caprolactone, f) 1,4-dioxepan-2-one, or g) 1,5-dioxepan-2-one.

Surgical devices prepared from the polymers and copolymers.

18 Claims, No Drawings

HOMOPOLYMERS AND COPOLYMERS OF SALICYLATE LACTONES

BACKGROUND OF THE INVENTION

Lactones and lactides, which are cyclic esters generally prepared by the condensation reaction of hydroxy acids or their derivatives, and polymerization products thereof, have been widely studied for numerous medical uses. For example, polymers derived from L-(−)-lactide, α-caprolactone, glycolide and p-dioxanone have been shown to have a wide variety of uses, including the preparation of various surgical devices such as sutures, suture coatings, surgical prostheses and implants, and as a carrier or matrix for sustained release of drugs. Many of these polymer compositions are advantageous for such medical uses because they are bioabsorbable and elicit minimal tissue reaction in animals.

In view of the demonstrated viability of using polymers derived from lactones and lactides for a variety of medical applications, there is a constant striving to develop new polymers and copolymers derived from such monomeric compounds. Accordingly, the development of these polymer systems is most desirable to advance the current state of the medical art.

SUMMARY OF THE INVENTION

In one aspect, the invention is a homopolymer of a monomer represented by the following formula:

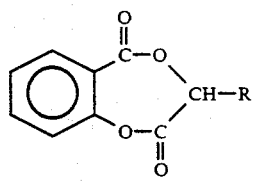

wherein R is hydrogen or methyl.

In another aspect, the invention is a copolymer of the monomer represented by the formula above and at least one of the following comonomers: a) glycolide, b) L-(−)-lactide, c) an alkylene carbonate, d) p-dioxanone, e) ε-caprolactone, f) 1,4-dioxepan-2-one, or g) 1,5-dioxepan-2-one.

Surprisingly, the homopolymer and copolymers of this invention are bioabsorbable. Significantly, these polymers can be processed to prepare bioabsorbable surgical devices, including such devices as surgical staples and bone pins. Additionally, the homopolymer and copolymers may find use in other areas of application for which absorbable polymers are used or the potential for use exists, especially uses related to the medical field.

DETAILED DESCRIPTION OF THE INVENTION a) Description of the Monomer

The monomer from which the homopolymer and copolymers of this invention are derived has the following formula:

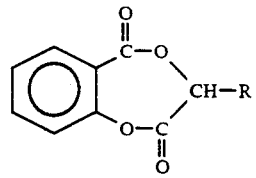

wherein R is hydrogen or methyl.

When R is hydrogen, the monomer is 1,4-benzodioxepin-2,5-(3-H)-dione. When R is methyl, the monomer is 1,4-benzodioxepin-2,5-(3-H, 3-methyl)-dione. Preferably, R is hydrogen. For purposes of describing this invention, both monomers will be referred to herein as glycosalicylate lactone monomers.

The glycosalicylate lactone monomers can be synthesized using the procedures described in U.S. Pat. No. 2,956,064. However, a more preferred procedure involves first reacting salicylic acid with an α-haloacetyl- or an α-halopropionyl halide (preferably either α-bromoacetyl- or α-bromopropionyl bromide), in the presence of a suitable organic base acting as an acid scavenger, e.g. triethylamine. The reaction medium is advantageously an anhydrous, nonreactive organic solvent such as chloroform or acetonitrile.

The resulting intermediate, a haloacetyl- or halopropionyl salicylic acid, is isolated, then dissolved in an anhydrous organic solvent and reacted with about 1 equivalent of triethylamine to form the closed ring structure of the glycosalicylate lactone monomer. The desired degree of monomer purity can be achieved by repeated recrystallization to remove unwanted excess reactants and byproducts, such as triethylammonium halide and hydroxylic species, e.g. water and alcohol.

The polymerization of the glycosalicylate lactone monomer proceeds by a ring opening reaction to yield repeating units represented by the following formula:

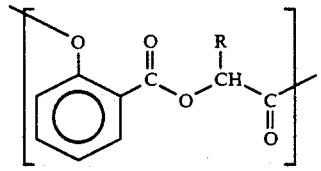

wherein R is hydrogen or methyl.

b) Description of the Homopolymer

For the preparation of high molecular weight homopolymers, the desired glycosalicylate lactone is advantageously recrystallized repeatedly to prepare a high-purity monomer. The monomer-grade glycosalicylate lactone is then polymerized in the presence of a conventional organometallic catalyst at a temperature above the melting temperature of the monomer, e.g. from about 115° to 160° C., for a time sufficient to achieve a desired viscosity. The time required for polymerization is highly dependent on polymerization temperature and can range from a few hours to a number of days.

Alternatively, it may be possible to prepare low molecular weight homopolymers by simply heating relatively impure glycosalicylate lactone, since the impurities present from the preparation of the monomer may initiate polymerization.

Preferably, the homopolymer of this invention exhibits an inherent viscosity of from about 0.1 to about 1.7 dL/g, more preferably from about 0.3 to about 1.4 dL/g, as measured in a 0.1 g/dL solution of hexafluoroisopropyl alcohol (HFIP) at 25° C. The glass transition temperature of the homopolymer preferably ranges from about 65° to about 80° C., and the melting temperature is preferably greater than 160° C. The homopolymer advantageously exhibits a degree of crystallinity as measured by x-ray diffraction greater than 5 percent, preferably greater than 25 percent, and more preferably greater than 30 percent. The specific properties desired depend significantly on the application for which the homopolymer is used, and these as well as other properties can be varied by adjusting the polymerization conditions.

The rate of degradation of the homopolymer in living tissue, commonly referred to as the bioabsorption profile in vivo, depends to a large degree on the molecular weight and percent crystallinity of the homopolymer. A strong indication of the bioabsorption profile in vivo can be determined by measuring the rate of degradation of the homopolymer in a phosphate buffer solution at elevated temperature. Generally, the rate of degradation can vary from about 20 to about 50 days for essentially complete degradation, or dissolution, in the phosphate buffer.

c) Description of the Copolymers

The copolymers of this invention preferably are prepared from a minor amount of the glycolsalicylate lactone monomer and a predominant amount of the desired comonomer component. In this manner, the properties of a polymer derived from the comonomer component can be modified and optimized.

The preferred comonomer components of the copolymers are glycolide and L-lactide, and the most preferred comonomer component is glycolide. The preferred amount of glycosalicylate lactone monomer from which the copolymers of this invention are prepared ranges from about 1 to about 35 weight percent, more preferably from about 5 to about 15 weight percent. The preferred alkylene carbonate comonomer component is trimethylene carbonate.

The copolymers can be prepared by polymerizing a mixture of the glycosalicylate lactone monomer and the selected comonomer component under conditions normally used for polymerizing the selected comonomer component. The physical and biological characteristics of the copolymers so prepared will depend significantly on those properties of polymers derived from the selected comonomer component.

d) Description of Processing and Preferred Uses for Homopolymers and Copolymers

The homopolymers and copolymers of this invention can be spun to prepare fibers or injection molded to prepare molded devices using conventional methods. In so doing, medical and surgical devices which are bioabsorbable and elicit minimal tissue reaction can be prepared. Such devices include surgical staples and bone pins or rods.

Copolymers incorporating the glycosalicylate lactone monomer can be tailor-made to fit specific applications by altering the properties of the commercially available polylactones and polylactides. For example, a copolymer of p-dioxanone or glycolide and the glycosalicylate lactone monomer can be prepared with an overall spectrum of different physical and biological properties than those obtained from polydioxanone or polyglycolide homopolymer.

Significantly, the homopolymer and copolymers of this invention may represent a new class of polymers which can withstand the detrimental effects of polymer degradation that often occurs during sterilization by irradiation with gamma rays. U.S. Pat. Nos. 4,435,590 and 4,510,295 describe the preparation of phenyl-substituted polymers which are radiation-sterilizable. These polymers are analogous to the homopolymers and copolymers of this invention because of the substituted benzene ring present in the repeating units of each of these polymer systems. Indeed, it may be quite possible to prepare conventional bioabsorbable polymers such as polylactide and polyglycolide which are tailor-made to become radiation-sterilizable by copolymerizing with the glycosalicylate lactone monomer or by blending such polymers with the homopolymer and copolymers of this invention.

The following examples illustrate the claimed invention. They should not be construed as limiting the claimed invention in any way, since one skilled in the art can readily foresee the preparation of homopolymers exhibiting different properties than those suggested by the examples, and the preparation of numerous copolymer systems all within the scope and teachings of this invention.

EXAMPLE 1

Synthesis of Bromoacetylsalicylic Acid 170.0 grams (1.23 moles) of salicylic acid and 620 mL of distilled chloroform were added to a two liter, three neck, round bottom flask equipped with a nitrogen gas inlet and outlet, a 250 mL pressure equalizing addition funnel, and a mechanical stirrer. The flask was chilled in an ice bath. 190 mL (1.36 moles) of distilled triethylamine was transferred into the addition funnel, and the whole system was flushed out with dry nitrogen gas. The triethylamine was added slowly over a ten minute period of time. The salicylic acid dissolved completely in the reaction mixture about half way through the addition. When the addition of triethylamine was over, the ice bath was removed. A thermometer was inserted into the reaction mixture, and the addition funnel was replaced by another 250 mL dropping funnel filled with a solution of 267.0 grams (1.32 moles) of distilled bromoacetyl bromide and 150 mL of distilled chloroform. The apparatus was flushed with dry nitrogen gas, and an inert atmosphere was maintained throughout the reaction. The flask was chilled with a dry ice/acetone bath down to −30° C., and then, the bromoacetyl bromide solution was added slowly over 10 minutes with vigorous stirring keeping the temperature below 0° C. The reaction mixture became a thick slurry after seven or eight minutes, and sometimes, mechanical stirring was not possible until the slurry warmed up to 5°-10° C. The dry ice bath was removed after the addition of the bromoacetyl bromide, and the reaction mixture was allowed to warm up to room temperature with stirring. After about 5.5 hours, the slurry was vacuum filtered. The filtercake was crude product that had crystallized out during the reaction. It was air dried in the Buchner funnel and weighed 224.5 grams. The filtrate contained both product, bromoacetylsalicyclic acid, and by-product, triethylammonium bromide.

The filtercake was dissolved in boiling chloroform. About 15 mL of ethanol was used to clarify the solution at the end of the dissolution process. The total volume was approximately 1150 mL. The hot solution was gravity filtered into a clean two liter Erlenmeyer flask. White needle-like crystals started to form after ten minutes. After standing at room temperature overnight, the crystals were isolated by suction filtration. The crystals were washed with 300 mL of a 2:1 solution of n-hexane and chloroform (vol/vol), air dried in the Buchner funnel, and vacuum dried at room temperature overnight (0.01 mm Hg). 100.5 grams of product were isolated in the first crop of crystals (31.6% yield so far). MP=138°-141° C. at 1.5° C./minute. The filtrate from the recrystallization was condensed down to about 150 mL on the rotary evaporator and then heated to reflux. About 10 mL of ethanol was added to clarify the boiling solution. The hot solution was gravity filtered into a clean 250 mL Erlenmeyer flask and allowed to recrystallize overnight at room temperature. Another 15.5 grams of product was isolated in this second crop as previously described. MP=136°-139° C. at 2° C./minute. Now the yield was 36.4%. The filtrate was discarded.

The filtrate from the reaction mixture was transferred into a two liter round bottom flask, and the solvent was removed by evaporation. A solid residue was left. 500 mL of acetone was added to the flask, and the suspension stirred overnight. Then, the insoluble material (Et$_3$NBr) was removed by suction filtration. The filtrate was transferred into a two liter round bottom flask, and the acetone was removed by evaporation. A brown solid was obtained. The brown solid was redissolved in 500 mL of acetone and diluted with 20 mL of ethanol. Some activated charcoal was added, and the suspension stirred overnight. The suspension was vacuum filtered through celite, and an orange transparent filtrate was obtained. The solvent was removed by evaporation, and the orangish white solid residue was dissolved in 400 mL of boiling chloroform. The volume was condensed to about 320 mL, and the solution was gravity filtered into a 500 mL Erlenmeyer flask. Recrystallization started within a few minutes. After standing at room temperature overnight, the crystals were isolated by vacuum filtration and washed with 200 mL of a 1:1 solution of n-hexane and chloroform (vol/vol). The white crystals were air dried and weighed 42.4 grams wet. The orange filtrate was discarded. The crystals were dissolved in 180 mL of hot chloroform. 20 mL of ethanol was also added to clarify the solution. After recrystallization at room temperature overnight, another 15.0 grams of product were recovered. MP=135°-142° C. at 2° C./minute. The total yield was 41.4% in three crops. IR (KBr pellet): 3440, 3300-2500 broad band, 1775, 1698, 1610, 1412, 1310, 1280, 1210, 1125, 770, 715, 585, 540 cm$^{-1}$. 300 MHz $^1$H NMR (CDCl$_3$): δ4.14 singlet (2H), δ7.19 doublet of doublets (1H), δ7.40 five intense lines (1H), δ7.64 seven intense lines (1H), δ8.14 doublet of doublets (1H). The carboxylic acid proton was not observed.

EXAMPLE 2

Synthesis of 1,4-Benzodioxepin-2,5-(3H)-dione 4.00 grams (15.4 mmoles) of bromoacetylsalicylic acid was dissolved in 40 mL of reagent grade acetone in a 250 mL, three neck round bottom flask containing a magnetic stir bar. The flask was equipped with a dry nitrogen gas inlet and outlet, a 100 mL pressure equalizing addition funnel, and a water cooled condenser. The flask was immersed in an oil bath set at 60° C., and the contents were heated to reflux. In the meantime, 1.56 grams (15.4 mmoles) of distilled triethylamine was dissolved in 20 mL of acetone and transferred into the addition funnel. The reaction vessel was thoroughly flushed with dry nitrogen gas, and an inert atmosphere was maintained throughout the reaction.

The triethylamine solution was added all at once to the refluxing solution of bromoacetylsalicylic acid. The addition took thirty seconds. Moments later, the by-product Et$_3$NHBr crystallized out of solution. The suspension was refluxed for one hour and then allowed to cool. The salt crystals were isolated by vacuum filtration, washed with 25 mL of acetone, air dried in the Bucher funnel, and finally vacuum dried at room temperature. 2.27 grams of triethylammonium bromide were collected. MP=249°-252° C. with decomposition. The filtrate was evaporated down, and a white solid was obtained which was then dissolved in 25 mL of boiling toluene. Everything did not dissolve. The hot toluene solution was gravity filtered into a 25 mL Erlenmeyer flask. A white solid started to crystallize after a few minutes. The insoluble material was soluble in water which strongly suggested that it was Et$_3$NHBr. After standing overnight at room temperature, the crystals were isolated by suction filtration, washed with 20 mL of toluene, and vacuum dried at room temperature for five hours. 1.17 grams were collected (43% yield). MP=112°-114° C. at 3.5° C./minute. IR (KBr pellet) 1795, 1730, 1605, 1455, 1315, 1190, 1120, 1025, 930, 763 cm$^{-1}$. 300 MHz $^1$H NMR (CDCl$_3$): δ4.75 singlet (2H), δ7.30 doublet (1H). One of the lines overlapped with the chloroform signal. δ7.42 triplet (1H), δ7.70 triplet (1H), δ7.95 doublet (1H).

Proton NMR also revealed the presence of 3% triethylammonium bromide as suggested by the triplet at δ1.44 and the quartet at δ3.13.

EXAMPLE 3

Polymerization of 1,4-Benzodioxepin-2,5-(3H)-dione

A sample of 1,4-benzodioxepin-2,5-(3H)-dione was recrystallized again from a mixture of ethanol and toluene. 1.17 grams were dissolved in a boiling solution of 5 mL of ethanol and 20 mL of toluene. The total volume was reduced to about 15 mL, and the hot solution was gravity filtered into a 25 mL Erlenmeyer flask. After 45 minutes, crystals were growing from the bottom of the flask. The flask was placed in the refrigerator overnight. The crystals were isolated by suction filtration, washed three times with 10 mL of toluene, and vacuum dried at room temperature overnight. 0.57 grams (49% recovery) were collected. MP=112°-113° C. at 3° C./minute.

300 MHz $^1$H NMR showed that the amount of triethylammonium bromide had been reduced to 1.5 mole percent. This twice recrystallized sample of 1,4-benzodioxepin-2,5-(3H)-dione was then polymerized in the melt. An initiator solution was prepared by dissolving 0.7655 grams (4.50 mmoles) of NaOPh•3H$_2$O and 1.026 grams (4.66 mmoles) of 15-crown-5 ether in enough ethanol to make 10 mL of solution. The solution was then gravity filtered into a clean 25 mL Erlenmeyer flask for storage.

A small ampoule containing a magnetic stirring bar was rinsed out with trimethylchlorosilane and dried overnight in the oven at 150° C. The ampoule was removed from the oven, and 6.0 μL of initiator solution (2.7 μmoles) were added with a microsyringe. The ampoule was attached to a vacuum manifold to remove the ethanol. After five minutes, 0.5012 grams (2.82 mmoles) of twice recrystallized 1,4-benzodioxepin-2,5-(3H)-dione was added. MP=111.5°–113.5° C. at 2° C./minute. The loaded ampoule was again attached to the vacuum manifold overnight to dry the monomer and to remove residual water and ethanol.

The vacuum was broken with dry nitrogen gas, and the ampoule was capped with a rubber septum. The septum was wired down, the inside of the ampoule was flushed again with dry nitrogen gas. The ampoule was then immersed in an oil bath set at 125° C. The monomer melted. The color of the liquid monomer changed from colorless to reddish orange in the beginning of the polymerization. After four minutes, the melt viscosity was high enough so that magnetic stirring was impossible. After fifteen minutes, the dark reddish orange polymer did not flow when the ampoule was turned upside down. The polymerization tube was then wrapped with aluminum foil and placed back in the oil bath for six hours.

The product was isolated by freezing the ampoule in liquid nitrogen, wrapping the cold ampoule with paper towel, and breaking the ampoule gently with a hammer. A small plug of polymer was obtained. It was orangish brown in color. IR (thin film cast from $CHCl_3$ solution): 1790, 1730, 1610, 1385, 1300, 1225, 1175, 1130, 1090, 760 $cm^{-1}$. 300 MHz $^1H$ NMR ($CDCl_3$): δ5.06 singlet (2H), δ7.12 doublet (1H), δ7.25 triplet (1H) overlapped with $CHCl_3$ signal, δ7.50 triplet (1H), and δ8.05 doublet (1H). By integration, the sample was 98 mole % polymer, 1.0 mole % 1,4-benzodioxepin-2,5-(3H)-dione, and 1.0 mole % triethylammonium bromide. 75 MHz $^{13}C$ [$^1H$] NMR ($CDCl_3$): δ61.5, 122.2, 123.9, 126.5, 132.3, 134.5, 150.1, 163.7, and 166.4. The $^{13}C$ [$^1H$] NMR spectrum supported an alternating copolymer microstructure as expected. $M_n=10,000$ and $M_w=16,000$ by GPC using poly(methyl methacrylate) standards in HFIP.

EXAMPLE 4

The Hydrolysis of Poly(1,4-Benzodioxepin-2,5-(3H)-dione) ("PGS")

100 milligrams of poly(glycolate-alt-salicylate) (PGS) were suspended in 100 mL of a phosphate buffer pH 7.27. The jar was placed in a water bath set at 50° C. It took 52 days for the PGS sample to swell, hydrolyze, and dissolve in the buffer.

EXAMPLE 5

Polymerization of 1,4-Benzodioxepin-2,5-(3H)-dione

The recrystallized products of 1,4-benzodioxepin-2,5-(3H)-dione from fifteen different reactions were combined and weighed 13.6 grams. They were dissolved in about 150 mL of boiling toluene, gravity filtered in an Erlenmeyer flask, and allowed to crystallize. After standing at room temperature overnight, the crystals were isolated by suction filtration, washed with toluene, and vacuum dried at room temperature for eighteen hours. The yield was 9.6 grams (71% recovery). MP=109°–111° C. at 2.5° C./minute.

3.00 grams of 1,4-benzodioxepin-2,5-(3H)-dione were melt polymerized as described previously using sodium phenoxide complexed with a crown ether except the temperature was 130° C. The polymerization was so rapid that it occurred before the sample had melted completely.

Another 3.00 grams of monomer were melt polymerized without adding any initiator. The polymerization was not as rapid as the sodium phenoxide initiated sample, but the polymer melt was viscous after ten minutes of reaction.

After four hours, both samples were removed from the oil bath and isolated by freezing in liquid nitrogen and breaking open the ampoules. Both polymers were orangish brown. $^1H$ NMR confirmed the chemical structures as before. Both samples had 2.5 mole % triethylammonium bromide and 0.8 mole % unreacted monomer. The first polymer had an inherent viscosity of 0.115 dL/g in HFIP, a number average molecular weight of 8,700, and a weight average molecular weight of 13,000 by GPC. The second had an inherent viscosity of 0.122 dL/g, a number average molecular weight of 8,500, and a weight average molecular weight of 13,000 by GPC. Clearly then, the residual amount of triethylammonium bromide can initiate the polymerization of 1,4-benzodioxepin-2,5-(3H)-dione and act as a chain transfer agent to reduce the molecular weight of the polyester (remember the $pk_a$'s of carboxylic acids and ammonium salts are about equal).

These PGS samples were combined and weighed 5.70 grams. They were dissolved in 250 mL of a 40:60 (v/v) solution of chloroform and dimethylformamide. This solution was filtered and then added dropwise into 2.5 liters of methanol in a stainless steel blender with vigorous stirring. Fine white particles precipitated out. This powder was isolated by suction filtration and vacuum dried at room temperature. Proton NMR showed the absence of triethylammonium bromide and DMF and the presence of some unknown impurities. For this reason, the PGS powder was extracted with methanol for 24 hours on a Soxhlet extractor and then vacuum dried at 50° C. for eighteen hours. The sample weighed 2.97 grams (52.1% recovery). It had a number average molecular weight of 8,400 and a weight average molecular weight of 10,000 by GPC. The glass transition temperature was 73° C. as measured by DSC under nitrogen at 20° C./minute. The decomposition temperature was 279° C. as determined by TGA under nitrogen.

EXAMPLE 6

Preparation of PGS (with no catalyst)

1,4-Benzodioxepin-2,5-(3H)-dione (1.0 grams, 5.6 mmoles), that had been purified by many recrystallizations, was heated and magnetically stirred in a flame and vacuum dried, partially evacuated, sealed 5 mL glass ampoule at 120° C. for 20 hours.

The inherent viscosity was 0.93 dL/g in HFIP at 25° C. Proton NMR analysis of this material showed the following molar composition: 86.1% polymer, 8.6% oligomer, and 5.3% monomer. A melting point of 165° C. was measured by DSC. A small amount of this polymer (0.46 grams) was heated at 90° C. for 16 hours under vacuum (<0.1 mm Hg pressure) in an attempt to remove the unpolymerized monomer. However, less than a 0.5% weight loss was observed. X-ray analysis of this heat treated sample indicated a 20% crystallinity level. These crystalline domains may be composed of oligomers and/or polymers.

EXAMPLE 7

Preparation of PGS (with stannous octoate)

1,4-Benzodioxepin-2,5-(3H)-dione (1.0 grams, 5.6 mmoles), that had been purified by several recrystallizations, and a catalytic amount of stannous octoate (0.17 mL of a 6.6 mM toluene solution, 1.1 μmoles) were heated and magnetically stirred in a flame and vacuum dried, partially evacuated, sealed 5 mL glass ampoule at 120° C. for 43 hours. The resulting polymer was isolated by chilling in liquid nitrogen. After drying the polymer under vacuum (<0.1 mm Hg pressure) at room temperature for 16 hours, its inherent viscosity was measured in HFIP at 25° C. and found to be 0.62 dL/g. An amount of this material (0.90 grams) was heated at 125° C. under vacuum (<0.1 mm Hg pressure) for 24 hours to remove any remaining monomer. A 5.0% weight loss was obtained. Proton NMR analysis showed the following molar composition: 92.6% polymer, 5.5% oligomer, and 1.9% monomer. This devolatilized material exhibited a $T_g$ of 57° C. and a $T_m$ of 163° C. as determined by DSC, and an 8% crystallinity level as measured by x-ray analysis.

EXAMPLE 8

Preparation of PGS (with stannous octoate)

1,4-Benzodioxepin-2,5-(3H)-dione (3.5 grams, 19.7 mmoles), that had been purified by a number of recrystallizations, and a catalytic amount of stannous octoate (0.60 mL of a 6.6 mM toluene solution, 3.9 μmoles) were heated and magnetically stirred in a flame and vacuum dried, partially evacuated, sealed 10 mL glass ampoule at 120° C. for 66.5 hours. The resulting opaque polymer was isolated by chilling in liquid nitrogen. After drying the polymer under vacuum (<0.1 mm Hg pressure) at room temperature for 16 hours, its inherent viscosity was measured in HFIP at 25° C. and found to be 1.00 dL/g. An amount of this material (2.24 grams) was heated at 125° C. under vacuum (<0.1 mm Hg pressure) for 18 hours to remove any remaining monomer. A 3.3% weight loss was obtained. This devolatilized material exhibited a $T_g$ of 57° C. and a $T_m$ of 168° C. as determined by DSC, and a 33% crystallinity level as measured by x-ray analysis.

EXAMPLE 9

Cobalt 60 Irradiation of Bulk PGS 1,4-Benzodioxepin-2,5-(3H)-dione (6.0 grams, 3.4 mmoles), that had been purified by successive solvent recrystallizations and finally purified by sublimation at 90° C., was heated and magnetically stirred in a flame and vacuum dried, partially evacuated, sealed 10 mL glass ampoule at 120° C. for 48 hours. The resulting polymer was isolated by chilling in liquid nitrogen. After drying under vacuum (<0.1 mm Hg pressure) at room temperature for 16 hours, this polymer exhibited an inherent viscosity of 0.39 dL/g in HFIP at 25° C.

About 0.5 grams of this material were placed in a screw-top glass vial and then subjected to 2.5 mRads of Co60 radiation. The inherent viscosity of this irradiated polymer was again 0.39 dL/g in HFIP at 25° C., indicating that little (if any) molecular weight degradation occurred during sterilization.

5.11 grams of the unirradiated polymer were heated at 125° C. under vacuum (<0.1 mm Hg pressure) for 21 hours to remove any residual monomer. A 1.6% weight loss was observed. The inherent viscosity of this devolatilized material was 0.40 dL/g in HFIP at 25° C. NMR analysis of the devolatilized polymer showed the following molar composition: 91.7% polymer, 1.4% oligomer, and 6.9% monomer.

EXAMPLE 10

In Vitro and In Vivo Degradation of PGS

Three PGS samples that had been synthesized by a process similar to that described in Example 8 (i.e. 120° C./64 hours with stannous octoate at a monomer/catalyst ratio of 5000/1) were combined and extruded in an Instron Capillary Rheometer. The amount and I.V. of each sample were as follows:

0.5 g, 0.63 dL/g
0.5 g, 0.71 dL/g
0.5 g, 0.74 dL/g

The extrusion conditions were as follows:
die diameter=20 mil
L/D=46.44
ram speed=0.1 cm/min
shear rate=77.94 sec$^{-1}$
temperature=170° C.
take up speed=13 ft./min.

The inherent viscosity of the resulting extrudate was measured twice and found to be on average 0.55 dL/g at 25° C. in HFIP. A 0.1004 gram piece of the unannealed extrudate was hydrolyzed in 100 mL of phosphate buffer pH 7.25 at 50° C. After 17 days only 2% of the extrudate mass remained. Some of the extrudate was carefully annealed on an annealing rack with slight tension at 95° C. The unsterilized, annealed extrudate was implanted in the ventral abdominal subcutis of rats as described in the following procedure:

METHOD

Nineteen Long-Evans rats (100 g, female) were used in the study. Two segments, approximately 2 cm in length were inserted into the ventral abdominal subcutis. The implants were placed parallel to and about 1.5 cm from the midline. Two rats per sample were killed after 1, 4, 8, 10, 12, 16, 20 and 26 weeks, with a few exceptions. When absorption was well advanced, a larger number of rats were killed.

The skin with the implantation sites was removed and dried. These preparations were examined and evaluated using both the dissecting and transmission microscopes. Estimates of the amount of implant remaining were based on the length of the implant or segments in the dried hide and comparing it with a four week old preparation. Because marked fragmentation occurred, 20 to 45 pieces per implant, as well as migration and clumping of the fragments, measurements of the total length were difficult and only rough estimates were made.

The observed in vivo absorption rate is listed below, expressed as the average % extrudate remaining after a given time.

| in vivo absorption rate | |
|---|---|
| % extrudate remaining | time (weeks) |
| 100 | 1 |
| 94 | 4 |
| 38 | 8 |
| 20 | 10 |
| 15 | 12 |
| 4 | 16 |
| 4 | 20 |
| 0 | 26 |

What is claimed is:
1. A homopolymer of a monomer represented by the following formula:

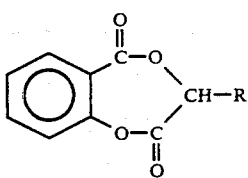

wherein R is hydrogen or methyl.

2. The homopolymer of claim 1 wherein R is hydrogen.

3. The homopolymer of claim 2 wherein the inherent viscosity of the homopolymer ranges from about 0.1 to about 1.7 dL/g.

4. The homopolymer of claim 3 wherein the inherent viscosity of the homopolymer ranges from about 0.3 to about 1.4 dL/g.

5. The homopolymer of claim 4 wherein the glass transition temperature of the homopolymer ranges from about 65° to about 80° C.

6. The homopolymer of claim 5 wherein the melting temperature of the homopolymer is greater than 160° C.

7. The homopolymer of claim 6 wherein the percent crystallinity of the homopolymer is greater than 5 percent.

8. The homopolymer of claim 7 wherein the percent crystallinity of the homopolymer is greater than 25 percent.

9. The homopolymer of claim 8 wherein the percent crystallinity of the homopolymer is greater than 30 percent.

10. A copolymer of the monomer represented by the formula of claim 1 and at least one of the following comonomers: a) glycolide, b) (L)-lactide, c) an alkylene carbonate, d) p-dioxanone, e) $\epsilon$-caprolactone, f) 1,4-dioxepan-2-one, or g) 1,5-dioxepan-2-one.

11. The copolymer of claim 10 wherein the comonomer is glycolide or L-lactide.

12. The copolymer of claim 11 wherein the comonomer is glycolide.

13. The copolymer of claim 12 wherein the amount of the monomer represented by the formula of claim 1 ranges from about 1 to about 35 weight percent.

14. The copolymer of claim 13 wherein the amount of the monomer represented by the formula of claim 1 ranges from about 5 to about 15 weight percent.

15. A surgical device prepared from the homopolymer of claim 1.

16. A surgical device prepared from the homopolymer of claim 9.

17. A surgical device prepared from the copolymer of claim 10.

18. A surgical device prepared from the copolymer of claim 14.

* * * * *